United States Patent [19]

Cicha et al.

[11] Patent Number: 5,773,637
[45] Date of Patent: Jun. 30, 1998

[54] PERFLUOROALKYL SULFONATES, THEIR PREPARATION AND USE

[75] Inventors: Walter Vladimir Cicha, Newark, Del.; Andreas Josef Kornath, Kamen, Germany; Ronald James McKinney; V. N. Mallikarjuna Rao, both of Wilmington, Del.; Joseph Stuart Thrasher; Alfred Waterfeld, both of Tuscaloosa, Ala.

[73] Assignee: E. I. du Pont de Nemours and Company, Wilmington, Del.

[21] Appl. No.: 708,997

[22] Filed: Sep. 6, 1996

[51] Int. Cl.$^6$ .................. C07F 9/00; C07F 7/00; C07F 9/70; C07F 7/22
[52] U.S. Cl. .................. 556/1; 556/42; 556/54; 556/56; 556/76; 556/81; 534/15; 562/899; 558/467; 570/165
[58] Field of Search .................. 556/42, 54, 56, 556/76, 81, 1; 534/15; 570/165; 558/467; 562/899

[56] References Cited

U.S. PATENT DOCUMENTS

| | | | |
|---|---|---|---|
| 3,496,217 | 2/1970 | Drinkard, Jr. et al. | 260/465.8 |
| 5,171,900 | 12/1992 | Eicher et al. | 570/168 |
| 5,283,381 | 2/1994 | Eicher et al. | 570/165 |

OTHER PUBLICATIONS

L.E. Manzer et al., *Adv. Catal.*, 39, 329–350, 1993.
George A. Olah et al., *Chemistry in Superacids. 61 a Perfluoroalkanesulfonic Acid–Boron Perfluoroalkanesulfonates; New Superacid Systems for Generation of Carbocations and Catalysts for Electrophilic Transformations of Hydrocarbons*, J. Org.Chem. 1984, 49,4591–4594.

Primary Examiner—Porfirio Nazario-Gonzalez

[57] ABSTRACT

A process is disclosed for preparing a perfluoroalkyl sulfonate of the formula $R_aMX_{b-c}O_g[(SO_3)_d(R_f)_e]_c$. This process involves reacting a reagent of the formula $R_aMX_bO_g$ and a second reagent of the formula $R'_xE[(SO_3)_d(R_f)_e]_y$, where R is selected from the group consisting of $C_1$ to $C_6$ alkyl, $C_1$ to $C_6$ perfluoroalkyl, cyclopentadienyl (i.e., $C_5H_5$), phenyl and perfluorophenyl;

M is selected from the group consisting of transistion metals of groups 3 to 12, main group elements of group 13 to 16 and lanthanide metals;

X is selected from the group consisting of F, Cl and Br;

$R_f$ is selected from the group consisting of $C_hF_{2h+1}$, $C_hF_{2h}$, wherein h is an integer from 0 to 10, perfluorophenyl, $C_6F_4(CF_2)_2i$, wherein i is an integer from 0 to 6, provided that when E is boron, $R_f$ is selected from the group consisting of $C_{h'}F_{2h'+1}$, wherein h' is an integer from 1 to 10, perfluorophenyl;

R' is selected from the group consisting of $C_jH_{2j+1}$, wherein j is an integer from 1 to 4, and phenyl;

E is selected from the group consisting of B and Si;

a is an integer from 0 to 3; b is an integer from 2 to 6; c is an integer from 1 to 6; d is an integer from 1 to 3; e is an integer from 1 to 4; g is an integer from 0 to 1; x is an integer from 0 to 3; and y is an integer from 1 to 3.

Novel perfluoroalkyl sulfonates are provided, as are methods which employ perfluoroalkyl sulfonates as catalysts for increasing the fluorine content of halogenated hydrocarbons and as promoters for hydrocyanation of olefins.

13 Claims, No Drawings

5,773,637

PERFLUOROALKYL SULFONATES, THEIR PREPARATION AND USE

This application claims the priority benefit of U.S. Provisional Application 60/004,066, filed Sept. 20, 1995 and U.S. Provisional Application 60/008, 035, filed Oct. 30, 1995.

FIELD OF THE INVENTION

This invention relates to perfluoroalkyl sulfonate compositions and their preparation, and use of such materials as catalysts for processing substituted hydrocarbons.

BACKGROUND

Numerous processes have been developed for increasing the fluorine content of halogenated hydrocarbons which are not fully fluorinated. Various catalysts have been proposed for use in facilitating hydrofluorination processes. See, e.g., L. E. Manzer et al., Adv. Catal. (39) pp. 329–350 (1993). For liquid-phase catalysed reactions, proposed catalysts include halides of metals such as antimony, boron, tantalum, niobium and molybdenum among others.

Fluorosulfonates of the formula $MX_n(FSO_3)_{5-n}$, where M is Ta or Nb, X is a halogen, and n is 0 to 4 have been disclosed as hydrofluorination catalysts (see U.S. Pat. No. 5,283,381). Mixtures of metal halides selected from the group consisting of niobium pentahalide, tantalum pentahalide, molybdenum pentahalide and mixtures thereof; and a sulfonic acid derivative selected from the group consisting of fluorosulfonic acid and $C_1$ to $C_4$ perfluoroalkyl sulfonic acids have also been disclosed as hydrofluorination catalysts (see U.S. Pat. No. 5,171,900). There is an interest in developing other liquid phase hydro-fluorination catalysts.

SUMMARY OF THE INVENTION

This invention provides a process for preparing a perfluoroalkyl sulfonate of the formula $R_aMX_{b-c}O_g[(SO_3)_d(R_f)_e]_c$. This process comprises reacting a reagent of the formula $R_aMX_bO_g$ and a second reagent of the formula $R'_xE[(SO_3)_d(R_f)_e]_y$, where R is selected from the group consisting of $C_1$ to $C_6$ alkyl, $C_1$ to $C_6$ perfluoroalkyl, cyclopentadienyl (i.e., $C_5H_5$), phenyl and perfluorophenyl;

M is selected from the group consisting of transistion metals of groups 3 to 12 such as Ti, Zr, Hf, V, Nb, Ta, Cr, Mo, and W; main group elements of group 13 to 16 such as Ge, Sn, Pb, Sb, As, and Bi; and lanthanide metals such as Ce and Pr;

X is selected from the group consisting of F, Cl and Br;

$R_f$ is selected from the group consisting of $C_hF_{2h+1}$, $C_hF_{2h}$ (i.e., a perfluoro group having two bonds), wherein h is an integer from 0 to 10, perfluorophenyl and $C_6F_4(CF_2)_{2i}$, wherein i is an integer from 0 to 6, provided that when E is boron, $R_f$ is selected from the group consisting of $C_{h'}F_{2h'+1}$, wherein h' is an integer from 1 to 10 and perfluorophenyl;

R' is selected from the group consisting of $C_jH_{2j+1}$, wherein j is an integer from 1 to 4, and phenyl;

E is selected from the group consisting of B and Si;

a is an integer from 0 to 3;

b is an integer from 2 to 6;

c is an integer from 1 to 6;

d is an integer from 1 to 3;

e is an integer from 1 to 4;

g is an integer from 0 to 1;

x is an integer from 0 to 3; and y is an integer from 1 to 3.

This invention further provides novel perfluoroalkyl sulfonate compositions selected from the group consisting of $TaCl_4(SO_3CF_3)$, $Ta_2F_5(SO_3CF_3)_5$, $TaF_2(SO_3CF_3)_3$, $NbCl_4(SO_3CF_3)$, $NbF_3(SO_3CF_3)_2$, $NbF_2(SO_3CF_3)_3$, $TiF_2(SO_3CF_3)_2$, $TiF_3(SO_3CF_3)$, $Ti_5Cl_{17}(SO_3CF_3)_3$, $Ti_5Cl_{12}(SO_3CF_3)_3$, $BiF_4(SO_3CF_3)$, $BiF_2(SO_3CF_3)_3$, $Bi(SO_3CF_3)_3$, $Pb_4F_5(SO_3CF_3)_3$, $Pb_5F_{17}(SO_3CF_3)_3$, $Sn_2F_7(SO_3CF_3)$, $TeF_2(SO_3CF_3)_2$, $ZrCl(SO_3CF_3)_3$, $CrF_2(SO_3CF_3)$, $AsF(SO_3CF_3)_2$, $AsF_2(SO_3C_4F_9)$, $As(SO_3CF_3)_3$, $BiF_2(SO_3CF_3)$, $SbF_2(SO_3CF_3)$, $SbF_3(SO_3CF_3)_2$, $Sb_2F(SO_3CF_3)_5$, $Ge_5F_{13}(SO_3CF_3)_7$, $MoCl_2(SO_3CF_3)_2$, $AsF_4(SO_3CF_3)$, $HfCl(SO_3CF_3)_3$, $V_2F_7(SO_3CF_3)$, $VO(SO_3CF_3)_3$, $VOF(SO_3CF_3)_2$, and $In_2Cl_3(SO_3CF_3)_3$.

This invention also provides a process for changing the fluorine content of a halogenated hydrocarbon containing from 1 to 6 carbon atoms, in the presence of a catalyst. This process is characterized by using a perfluoroalkyl sulfonate of the formula $R_aMX_{b-c}O_g[(SO_3)_d(R_f)_e]_c$ as a catalyst.

This invention also provides a process for hydrocyanation of an olefin (e.g., $CH_3CH=CHCH_2CN$) in the presence of a catalyst and a promoter. This process is characterized by using a perfluoroalkylsulfonate of the formula $R_aMX_{b-c}O_g[(SO_3)_d(R_f)_e]_c$ as a promoter.

DETAILED DESCRIPTION

The catalytic process of this invention for changing the fluorine content of halogenated hydrocarbons containing from 1 to 6 carbon atoms employs a perfluoroalkyl sulfonate catalyst which may be prepared as described herein. Preferably the perfluoroalkyl sulfonate is isolated prior to use as a catalyst. Of note are embodiments which employ a novel perfluoroalkyl sulfonate selected from the group provided above.

Reagents of the formula $R_aMX_bO_g$, where R is selected from the group consisting of $C_1$ to $C_6$ alkyl, $C_1$ to $C_6$ perfluoroalkyl, cyclopentadienyl, phenyl and perfluorophenyl; wherein a is an integer from 0 to 3; M is selected from the group consisting of transistion metals of groups 3 to 12 such as Sc, Y, La, Ti, Zr, Hf, V, Nb, Ta, Cr, Mo, W, Mn, Re, Co, Rh, Ir, Ni, Pd, Pt, Cu, Ag, Au, Zn, Cd and Hg; main group elements of group 13 to 16 such as Al, Ga In, Ti, Ge, Sn, Pb, Sb, Bi and As; lanthanide metals such as Ce and Pr; X is selected from the group consisting of F, Cl and Br; and b is an integer from 2 to 6 are commercially available. They can also be prepared by conventional techniques of halogenating the corresponding oxide. Generally, this reagent is introduced under inert atmospheric conditions, (i.e., in the absence of oxygen and water) into a glass, fluoropolymer or metal reactor.

The second reagent of this invention can be a silyl reagent of the formula $R'_3Si[(SO_3)_d(R_f)_e]$; where R' is selected from the group consisting of $C_jH_{2j+1}$, wherein j is an integer from 1 to 4, and phenyl; and $R_f$ is selected from the group consisting of $C_hF_{2h+1}$, wherein h is an integer from 0 to 6, $C_hF_{2h}$ (i.e., a perfluoroalkylene group), perfluorophenyl, and $C_6F_4(CF_2)_{2i}$, wherein i is an integer from 0 to 6. Typically the silyl reagent is slowly vacuum distilled into the reactor. Silyl reagents of this type are commercially available. They can also be prepared by known preparation techniques.

With silyl reagents, the order of reagent addition is considered important for controlling the number of $(SO_3)_d(R_f)_e$ ligands from 1 to 6 that are substituted on M for X, and for the simplification of product isolation and purification. As the silyl reagent is usually the more volatile reagent, it is typically added in slight excess. The degree of ligand substitution can also be affected by the relative amount of reagents used, the reaction temperature and the reaction duration, as described later. An inert solvent (typically $CH_3CN$, $SO_2$, $SO_2ClF$, or $HSO_3CF_3$) can be added if the reaction does not proceed over a period of a few hours, due to insufficient reactant miscibility. This inert solvent should be aprotic, non-hydrolyzing and low in basicity. The HF reagents are agitated from a few minutes to a few days at temperatures generally in the range of from 0° to 350° C., but preferably between 0° and 100° C. Ultrasound also can be used to enhance the reaction rates. It also is advantageous to remove the volatile by-product, $R'_3SiX$, to maintain an efficient reaction rate. The desired product can be isolated by removal of the by-products using standard distillation, filtration, crystallization, or extraction techniques. Distillation is usually the most suitable isolation technique. Purification of the desired solid product can be carried out by washing, recrystallization, or sublimation.

The second reagent can also be a boron reagent of the formula $B(SO_3R_f)_3$, where $R_f$ is selected from the group consisting of $C_kF_{2k+1}$, wherein k is an integer from 1 to 6, and perfluorophenyl. These reagents can be prepared in accordance with the chemistry described in G. A. Olah et al., J. Org. Chem. 49,4591 (1984). For embodiments employing such boron reagents, $R_aMX_bO_g$ may be introduced under inert (i.e., in the absence of oxygen and water) atmospheric conditions into a glass, fluoropolymer or metal reactor. The boron reagent $B(SO_3R_f)_3$ can then be charged into the reactor at stoichiometric amounts, which depend on the number of $SO_3R_f$ ligands from 1 to 6 that are desired to be substituted for X on M. Reaction temperature and time also are employed to control this degree of substitution. The order of reactant addition is not considered important. If the $R_aMX_bO_g$ reagent is volatile, the progress of the reaction is easier to control. An inert solvent, typically but not only $SO_2$ or $SO_2ClF$, should be introduced to the reaction to afford efficient mixing of the reactants. The reagents are agitated from a few hours to a few days at temperatures in the range of from about 0° to 90° C. ($B(SO_3R_f)_3$ will decompose above 95° C.), and preferably at or slightly above room temperature. Generally, the degree of substitution increases with increasing temperature and time. Ultrasound also can be used for reaction rate enhancement. It is advantageous to remove the volatile by-products, $BX_3$, to maintain an efficient reaction rate. The desired product is isolated by removal of the by-products by standard distillation, filtration, crystallization, or extraction techniques. Distillation to remove solvent is usually the method of choice for product isolation. Purification of the desired solid product can be carried out by washing, recrystallization, or sublimation.

Of note are reactions wherein the molar ratio of $R'_xE[(SO_3)_d(R_f)_e]_y$ to $R_aMX_bO_g$ is about c:1 when E is silicon or about c:3 when E is boron (where as noted above c is an integer from 1 to 6). Also of note are embodiments where g is 0, x is 3, and y is 1; and embodiments where g is 1, x is 3 and y is 1.

Included in this invention is a process for increasing the fluorine content of a saturated or olefinic compound having the formula $C_jH_kCl_pF_m$ where j is an integer from 1 to 6, k is an integer from 0 to 12, p is an integer from 0 to 13, m is an integer from 0 to 13, provided that p is at least 1 when the compound is saturated, by reacting said compound with HF in the liquid phase in the presence of the perfluoroalkyl sulfonate catalysts of this invention. Of note are embodiments where g is 0 and e is 3. The reaction of said compounds of the formula $C_jH_kCl_pF_m$ with HF in the presence of the catalysts of the instant invention is typically conducted at a temperature in the range of about 50° C. to about 175° C., preferably, 60° C. to 150° C. The pressure is selected so that the the reaction medium is maintained in the liquid state, typically between 101 kPa and 5000 kPa, preferably, 1135 kPa to 3203 kPa. For example, 1,1,1,3,3,3-hexachloropropane (HCC-230fa) can be reacted with HF in the liquid phase using the perfluoroalkyl sulfonate catalysts of the herein described invention such as those containing elements from the group consisting of titanium, hafriium, vanadium, niobium, tanatalum, chromium, molybdenum, tungsten, germanium, tin, lead, arsenic, antimony and bismuth to produce 3,3-dichloro-1,1,1,3-tetrafluoropropane (HCFC-234fb), 3-chloro-1,1,1,3,3-pentafluoropropane (HCFC-235fa) and 1,1,1,3,3,3-hexafluoropropane (HFC-236fa) and mixtures thereof. Both HCFC-234fb and HCFC-235fa can be hydrodechlorinated using a hydrodehalogenation catalyst to produce 1,1,1,3-tetrafluoropropane (HFC-254fb) and 1,1,1,3,3-pentafluoropropane (HFC-235fa), respectively. Palladium on acid-washed carbon is a preferred catalyst for the conversions of HCFC-234fb to HFC-254fb and HCFC-235fa to HFC-235fa.

The catalytic process of this invention for hydrocyanation of olefins employs a perfluoroalkyl sulfonate promoter which may be prepared as described herein (e.g., $Sn(SO_3CF_3)_4$, $CrF_2(SO_3CF_3)$ or $TiF_2(SO_3CF_3)_2$). Preferably the perfluoroalkyl sulfonate is isolated prior to use as a promoter. Of note are embodiments which employ a novel perfluoroalkyl sulfonate selected from the group provided above. Also of note are embodiments where g is 0 and e is 3. The hydrocarbon may be conducted in accordance with conventional process conditions (see e.g., U.S. Pat. No. 3,496,217). Typically, a nickel catalyst is employed.

The invention is further illustrated in the following non-limiting examples.

The novel compositions listed as Examples 1–37 in the two Tables that follow are amongst those that were prepared using triflating reagents with E=silicon or E=boron, in accordance with the reactions described above. Typical reaction conditions are provided.

TABLE 1

| | (Silyl Reagent Used) | | | | |
|---|---|---|---|---|---|
| Ex. | Perfluoroalkyl sulfonate | Reaction Time (hr) | Reaction Temp. (°C.) | $MX_bO_g$ (mmol) | Second Reagent (mmol) | Analytical Method |
| 1[b] | $AsF(OTf)_2$[a] | 24–48 | 25 | $AsF_3$ (4.02) | $(CH_3)_3SiOTf$ (12.10) | microanalysis, FT-Raman, $^{19}F$- and $^{13}C$-NMR |
| 2 | $AsF_2(SO_3C_4F_9)$ | 220 | 25–60 | $AsF_3$ (18.3) | $(CH_3)_3Si$(n- | m.p., $^{19}F$-NMR |

TABLE 1-continued (Silyl Reagent Used)

| Ex. | Perfluoroalkyl sulfonate | Reaction Time (hr) | Reaction Temp. (°C.) | $MX_bO_g$ (mmol) | Second Reagent (mmol) | Analytical Method |
|---|---|---|---|---|---|---|
| | | | | | $C_4F_9SO_3$) (10.1) | |
| 3 | $AsF_4(OTf)$ | 24 | 25 | $AsF_5$ (2.59) | $(CH_3)_3SiOTf$ (13.0) | m.p., FT-Raman |
| 4[c] | $BiF_2(OTf)$ | 24 | 25 | $BiF_3$ (2.37) | $(CH_3)_3SiOTf$ (7.11) | FT-IR, FT-Raman |
| 5[c] | $Bi(OTf)_3$ | 20 | 25 | $BiF_3$ (2.00) | $(CH_3)_3SiOTf$ (7.17) | microanalysis |
| 6 | $BiF_4(OTf)$ | 72 | 25 | $BiF_5$ (0.69) | $(CH_3)_3SiOTf$ (3.50) | microanalysis, FT-Raman |
| 7 | $SbF_2(OTf)$ | 24 | 25 | $SbF_3$ (2.85) | $(CH_3)_3SiOTf$ (8.55) | microanalysis, FT-IR, FT-Raman |
| 8[d] | $Sb_2F(OTf)_5$ | 120 | 25 | $SbF_3$ (4.87) | $(CH_3)_3SiOTf$ (14.60) | FT-IR |
| 9 | $SbF_3(OTf)_2$ | 24 | 25 | $SbF_5$ (2.49) | $(CH_3)_3SiOTf$ (25.0) | $^{19}$F-NMR |
| 10 | $CrF_2(OTf)$ | 120 | 25 | $CrF_3 \cdot 4H_2O$ (41.8) | $(CH_3)_3SiOTf$ (158) | FT-IR |
| 11 | $TiF_2(OTf)_2$ | 18 | 25 | $TiF_4$ (2.99) | $(CH_3)_3SiOTf$ (12.69) | microanalysis, FT-IR, FT-Raman |
| 12 | $TiF_3(OTf)$ | 24 | 60 | $TiF_2(OTf)_2$,[e] (0.56) | $HF^e$ (10.0) | FT-IR |
| 13 | $Ti_5Cl_{17}(OTf)_3$ | 19 | 25 | $TiCl_4$ (15.7) | $(CH_3)_3SiOTf$ (15.3) | FT-IR |
| 14 | $Ti_5Cl_{12}(OTf)_3$ | 24 | 25 | $TiCl_3$ (2.33) | $(CH_3)_3SiOTf$ (7.00) | FT-IR |
| 15 | $HfCl(OTf)_3$ | 27 | 25 | $HfCl_4$ (2.93) | $(CH_3)_3SiOTf$ (11.72) | m.p., FT-IR, FT-Raman |
| 16 | $NbCl_4(OTf)$ | 6–24 | 25–90 | $NbCl_5$ (3.29) | $(CH_3)_3SiOTf$ (16.4) | FT-Raman, $^{19}$F-NMR |
| 17 | $NbF_3(OTf)_2$ | 5 | 25 | $NbF_5$ (2.82) | $(CH_3)_3SiOTf$ 14.1 | FT-Raman, FT-IR |
| 18 | $NbF_2(OTf)_3$ | 72 | 65 | $NbF_5$ (0.80) | $(CH_3)_3SiOTf$ (5.58) | $^{19}$F-NMR |
| 19 | $TaF_2(OTf)_3$ | 11–24 | 60–70 | $TaF_5$ (20.9) | $(CH_3)_3SiOTf$ (103) | mp, FT-Raman |
| 20 | $Ta_2F_5(OTf)_5$ | 24 | 25 | $TaF_5$ (2.83) | $(CH_3)_3SiOTf$ (14.9) | mp, FT-Raman, FT-IR |
| 21 | $TaCl_4(OTf)$ | 24 | 25 | $TaCl_5$ (5.16) | $(CH_3)_3SiOTf$ (33.5) | mp, $^{19}$F-NMR, FT-Raman, FT-IR |
| 22 | $Sn_2F_7(OTf)$ | 30 | 25 | $SnF_4$ (0.92) | $(CH_3)_3SiOTf$ (3.91) | FT-IR |
| 23 | $Mo_5Cl_{12}(OTf)_8$ | 24 | 25 | $MoCl_4$ (0.25) | $(CH_3)_3SiOTf$ (1.01) | FT-IR, $^{19}$F-NMR |
| 24 | $In_2Cl_3(OTf)_3$ | 96 | 25 | $InCl_3 \cdot 4H_2O$ (2.18) | $(CH_3)_3SiOTf$ (14.83) | FT-IR |
| 25 | $Ge_5F_{13}(OTf)_7$ | 0.5 | 25 | $GeF_4$ (4.04) | $(CH_3)_3SiOTf$ (16.15) | FT-IR |
| 26 | $Pb_4F_5(OTf)_3$ | 20 | 25 | $PbF_2$ (4.20) | $(CH_3)_3SiOTf$ (8.40) | mp, FT-IR |
| 27 | $Pb_5F_{17}(OTf)_3$ | 72 | 25 | $PbF_4$ (5.43) | $(CH_3)_3SiOTf$ (10.86) | FT-IR |
| 28 | $TeF_2(OTf)_2$ | 48 | 25 | $TeF_4$ (1.67) | $(CH_3)_3SiOTf$ (10.03) | FT-IR |
| 29 | $V_2F_7(OTf)$ | 48 | 25 | $VF_4$ (3.62) | $(CH_3)_3SiOTf$ (14.50) | FT-IR |
| 30 | $VO(OTf)_3$ | 72 | 25 | $VOF_3$ (1.13) | $(CH_3)_3SiOTf$ (9.04) | FT-IR |
| 31 | $VOF(OTf)_2$ | 24 | 25 | $VOF_3$ (0.81) | $(CH_3)_3SiOTf$ (4.03) | $^{19}$F-NMR |
| 32 | $ZrCl(OTf)_3$ | 24 | 25 | $ZrCl_4$ (2.19) | $(CH_3)_3SiOTf$ (8.76) | m.p., FT-IR |

[a]OTf is $SO_3CF_3$
[b]$AsF(OTf)_2$ was prepared either in a neat reaction or in acetonitrile solvent
[c]$CF_3SO_3H$ was used as a solvent
[d]Acetonitrile was used as a solvent
[e]See Example 11

TABLE 2

| | | | | (Boron Reagent Used) | | | |
|---|---|---|---|---|---|---|---|
| Ex. | Perfluoroalkyl sulfonate | Reaction Time (hr) | Reaction Temp. (°C.) | $MX_b$ (mmol) | $B(SO_3CF_3)_3$ (mmol) | Solvent | Analytical Method |
| 33 | $AsF_4(OTf)$ | 92 | 25 | $AsF_5$ (3.56) | 5.94 | $SO_2$ | FT-IR |
| 34 | $As(OTf)_3$ | 96 | 25 | $AsF_3$ (0.87) | 0.87 | $SO_2ClF$ | m.p., FT-IR, $^{19}F$- and $^{13}C$-NMR |
| 35 | $TaF_2(OTf)_3$ | 192 | 25 | $TaF_5$ (1.09) | 1.81 | $SO_2ClF$ | microanalysis, m.p., FT-IR, $^{19}F$- and $^{13}C$-NMR |
| 36 | $NbF_3(OTf)_2$ | 144 | 25 | $NbF_5$ (2.66) | 2.66 | $SO_2ClF$ | m.p., FT-IR |
| 37 | $BiF_2(OTf)_3$ | 120 | 25 | $BiF_5$ (1.65) | 1.65 | $SO_2ClF$ | microanalysis, m.p., FT-IR, $^{19}F$- and $^{13}C$-NMR |

EXAMPLE 38

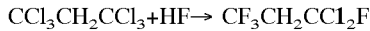
$CCl_3CH_2CCl_3 + HF \rightarrow CF_3CH_2CCl_2F$

To a 450 mL Hastelloy® nickel alloy autoclave provided with an agitator, chilled water condenser operating at −15° C. and a back-pressure regulator was charged 100 g $CCl_3CH_2CCl_3$ (230 fa) and 2.5 g of $TiF_2(SO_3CF_3)_2$. The autoclave was sealed and cooled in dry ice. Into the chilled autoclave was condensed, 100 g of anhydrous HF. The back-pressure regulator was set at 500 psig (3548 kPa). The autoclave and contents were brought to room temperature and then slowly heated with stirring to 100°C. (internal temperature) using an electrical heater. After 24 hours at these conditions, the area % product composition was 1.7% $CF_3CH_2CClF_2$, 91.1% $CF_3CH_2CCl_2F$ and 5.1% $CF_3CH_2CCl_3$.

EXAMPLE 39

$CH_3CH=CHCH_2CN + HCN \rightarrow NC(CH_2)_4CN$

A glass reactor fitted with a nitrogen bubbler was charged with 3-pentenenitrile (5 mL; 52 mmol), ligand A, the structure of which is shown below, (0.354 g; 0.45 mmol), $Ni(COD)_2$ (0.040 g; 0.15 mmol) and $Sn(SO_3CF_3)_4$ (0.107 g; 0.15 mmol) under inert nitrogen atmosphere. The mixture was heated to 70° C. and agitated with a magnetic stirrer. HCN was delivered to the reactor by sparging a source of liquid HCN (cooled to 0°C.) with 30 mL/min of dry nitrogen and directing the resulting saturated $HCN/N_2$ mixture into the reactor below the liquid level. Progress of the reaction was monitored by removing aliquots and analyzing by gas chromatography (GC). After 1 hr the reaction was terminated and GC analysis revealed a 3-pentenenitrile conversion to dinitriles (these include methylglutaronitrile and ethylsuccinonitrile) of 80% and an adiponitrile (ADN) yield of 80% (where conversion is total dinitriles/initial pentenenitriles; and ADN yield is ADN/total dinitriles). COD is cyclooctadiene. Ligand A structure:

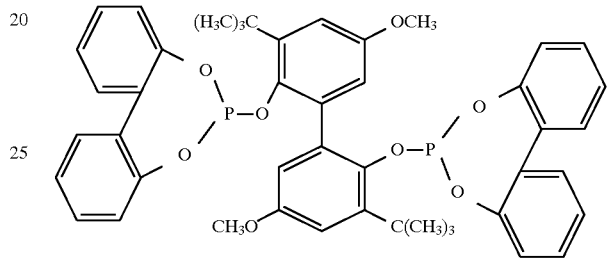

We claim:

1. A process for preparing a perfluoroalkyl sulfonate of the formula
   $R_aMX_{b-c}O_{gc}$, comprising:
   reacting a reagent of the formula $R_aMX_bO_g$ and a second reagent of the formula $R'_xE[(SO_3)_d(R_f)_e]_y$, where R is selected from the group consisting of $C_1$ to $C_6$ alkyl, $C_1$ to $C_6$ perfluoroalkyl, cyclopentadienyl, phenyl and perfluorophenyl;
   M is selected from the group consisting of transistion metals of groups 3 to 12, main group elements of group 13 to 16, and lanthanide metals;
   X is selected from the group consisting of F, Cl and Br;
   $R_f$ is selected from the group consisting of $C_{h'}F_{2h'+1}$, wherein h' is an integer from 1 to 10, and perfluorophenyl;
   R' is selected from the group consisting of $C_jH_{2j+1}$, wherein j is an integer from 1 to 4, and phenyl;
   E is B;
   a is an integer from 0 to 3;
   b is an integer from 2 to 6;
   c is an integer from 1 to 6;
   d is an integer from 1 to 3;
   e is an integer from 1 to 4;
   g is an integer from 0 to 1;
   x is an integer from 0 to 3; and
   y is an integer from 1 to 3.
2. The process of claim 1 wherein the second reagent is a boron reagent of the formula $B(SO_3R_f)_3$, where $R_f$ is selected from the group consisting of $C_kF_{2k+1}$, wherein k is an integer from 1 to 6, and perfluorophenyl.
3. A process for changing the fluorine content of a halogenated hydrocarbon containing from 1 to 6 carbon atoms, in the presence of a catalyst, characterized by:
   using a perfluoroalkyl sulfonate of the formula $R_aXM_{b-c}O_{gc}[(SO_3)_d(R_f)_e]_e$ prepared in accordance with claim 1 as a catalyst.

4. The process of claim 3 wherein the perfluoroalkyl sulfonate is selected from the group consisting of $TaCl_4(SO_3CF_3)$, $Ta_2F_5(SO_3CF_3)_5$, $TaF_2(SO_3CF_3)_3$, $NbCl_4(SO_3CF_3)$, $NbF_3(SO_3CF_3)_2$, $NbF_2(SO_3CF_3)_3$, $TiF_2(SO_3CF_3)_2$, $TiF_3(SO_3CF_3)$, $Ti_5Cl_{17}(SO_3CF_3)_3$, $Ti_5Cl_{12}(SO_3CF_3)_3$, $BiF_4(SO_3CF_3)$, $BiF_2(SO_3CF_3)_3Bi(SO_3CF_3)_3$, $Pb_4F_5(SO_3CF_3)_3$, $Pb_5F_{17}(SO_3CF_3)_3$, $Sn_2F_7(SO_3CF_3)$, $TeF_2(SO_3CF_3)_2$, $ZrCl(SO_3CF_3)_3$, $CrF_2(SO_3CF_3)$, $AsF(SO_3CF_3)_2$, $AsF_2(SO_3C_4F_9)$, $As(SO_3CF_3)_3$, $BiF_2(SO_3CF_3)$, $SbF_2(SO_3CF_3)$, $SbF_3(SO_3CF_3)_2$, $Sb_2F(SO_3CF_3)_5$, $Ge_5F_{13}(SO_3CF_3)_7$, $MoCl_2(SO_3CF_3)_2$, $AsF_4(SO_3CF_3)$, $HfCl(SO_3CF_3)_3$, $V_2F_7(SO_3CF_3)$, $VO(SO_3CF_3)_3$, $VOF(SO_3CF_3)_2$, and $In_2Cl_3(SO_3CF_3)_3$.

5. The process of claim 4 wherein the perfluoroalkyl sulfonate is isolated prior to use as a catalyst.

6. A process for changing the fluorine content of a halogenated hydrocarbon containing from 1 to 6 carbon atoms, in the presence of a catalyst, characterized by:

using a perfluoroalkyl sulfonate of the formula $R_aXM_{b-c}O_{gc}[(SO_3)_d(R_f)_e]_e$ as a catalyst, where R is selected from the group consisting of $C_1$ to $C_6$ alkyl, $C_1$ to $C_6$ perfluoroalkyl, cyclopentadienyl, phenyl and perfluorophenyl;

M is selected from the group consisting of transistion metals of groups 3 to 12, main group elements of group 13 to 16, and lanthanide metals;

X is selected from the group consisting of F, Cl and Br;

$R_f$ is selected from the group consisting of $C_hF_{2h+1}$, $C_hF_{2h}$, wherein h is an integer from 0 to 10, perfluorophenyl, $C_6F_4(CF_2)_{2i}$, wherein i is an integer from 0 to 6, provided that when E is boron, $R_f$ is selected from the group consisting of $C_{h'}F_{2h'+1}$, wherein h' is an integer from 1 to 10, and perfluorophenyl;

R' is selected from the group consisting of $C_jH_{2j+1}$, wherein j is an integer from 1 to 4, and phenyl;

E is selected from the group consisting of B and Si;

a is an integer from 0 to 3;

b is an integer from 2 to 6;

c is an integer from 1 to 6;

d is an integer from 1 to 3;

e is an integer from 1 to 4; and g is an integer from 0 to 1.

7. The process of claim 5 wherein the halogenated hydrocarbon is a saturated or olefinic compound having the formula $C_jH_kCl_pF_m$ where j is an integer from 1 to 6, k is an integer from 0 to 12, p is an integer from 0 to 13, m is an integer from 0 to 13, provided that p is at least 1 when the compound is saturated; and wherein the halogenated hydrocarbon is reacted with HF in the liquid phase in the presence of the perfluoroalkyl sulfonate catalyst.

8. The process of claim 7 wherein the halogenated hydrocarbon is $CCl_3CH_2CCl_3$.

9. The process of claim 8 wherein $CF_3CH_2CCl_2F$ is produced.

10. The process of claim 9 wherein the perfluoroalkyl sulfonate catalyst is $TiF_2(SO_3CF_3)_2$.

11. A process for hydrocyanation of an olefin in the presence of a catalyst and a promoter, characterized by:

using a perfluoroalkyl sulfonate of the formula $R_aXM_{b-c}O_{gc}$ prepared in accordance with claim 1 as a promoter.

12. The process of claim 11 wherein the olefrn is $CH_3CH=CHCH_2CN$.

13. A perfluoroalkyl sulfonate selected from the group consisting of $TaCl_4(SO_3CF_3)$, $Ta_2F_5(SO_3CF_3)_5$, $TaF_2(SO_3CF_3)_3$, $NbCl_4(SO_3CF_3)$, $NbF_3(SO_3CF_3)_2$, $NbF_2(SO_3CF_3)_3$, $TiF_2(SO_3CF_3)_2$, $TiF_3(SO_3CF_3)$, $Ti_5Cl_{17}(SO_3CF_3)_3$, $Ti_5Cl_{12}(SO_3CF_3)_3$, $BiF_4(SO_3CF_3)$, $BiF_2(SO_3CF_3)_3$, $Bi(SO_3CF_3)_3$, $Pb_4F_5(SO_3CF_3)_3$, $Pb_5F_{17}(SO_3CF_3)_3$, $Sn_2F_7(SO_3CF_3$, $TeF_2(SO_3CF_3)_2$, $ZrCl(SO_3CF_3)_3$, $CrF_2(SO_3CF_3)$, $AsF(SO_3CF_3)_2$, $AsF_2(SO_3C_4F_9)$, $As(SO_3CF_3)_3$, $BiF_2(SO_3CF_3)$, $SbF_2(SO_3CF_3)$, $SbF_3(SO_3CF_3)_2$, $Sb_2F(SO_3CF_3)_5$, $Ge_5F_{13}(SO_3CF_3)_7$, $MoCl_2(SO_3CF_3)_2$, $AsF_4(SO_3CF_3)$, $HfCl(SO_3CF_3)_3$, $V_2F_7(SO_3CF_3)$, $VO(SO_3CF_3)_3$, $VOF(SO_3CF_3)_2$, and $In_2Cl_3(SO_3CF_3)_3$.

* * * * *

UNITED STATES PATENT AND TRADEMARK OFFICE
CERTIFICATE OF CORRECTION

PATENT NO. : 5,773,637
DATED : June 30, 1998
INVENTOR(S) : Cicha, et al

It is certified that error appears in the above-identified patent and that said Letters Patent is hereby corrected as shown below:

Column 9, line 16, delete claim 6, and insert the following:

-- 6. A process for changing the fluorine content of a halogenated hydrocarbon containing from 1 to 6 carbon atoms, in the presence of a catalyst, characterized by:

using a perfluoroalkyl sulfonate of the formula $R_a X M_{b-c} O_g [(SO_3)_d (R_f)_e]_c$ as a catalyst, where R is selected from the group consisting of $C_1$ to $C_6$ alkyl, $C_1$ to $C_6$ perfluoroalkyl, cyclopentadienyl, phenyl and perfluorophenyl;

M is selected from the group consisting of transistion metals of groups 3 to 12, main group elements of group 13 to 16, and lanthanide metals;

X is selected from the group consisting of F, Cl and Br;

$R_f$ is selected from the group consisting of $C_h F_{2h+1}$, $C_h F_{2h}$, wherein h is an integer from 0 to 10, perfluorophenyl, $C_6 F_4 (CF_2)_{2i}$, wherein i is an integer from 0 to 6

UNITED STATES PATENT AND TRADEMARK OFFICE
CERTIFICATE OF CORRECTION

PATENT NO. : 5,773,637
DATED : June 30, 1998
INVENTOR(S) : Cicha, et al

It is certified that error appears in the above-identified patent and that said Letters Patent is hereby corrected as shown below:

```
a is an integer from 0 to 3;
b is an integer from 2 to 6;
c is an integer from 1 to 6;
d is an integer from 1 to 3;
e is an integer from 1 to 4; and
g is an integer from 0 to 1.
```

Signed and Sealed this

Sixteenth Day of March, 1999

Attest:

Attesting Officer

Q. TODD DICKINSON

Acting Commissioner of Patents and Trademarks